United States Patent [19]

Schulman et al.

[11] 4,027,677
[45] June 7, 1977

[54] MYOCARDIAL LEAD

[75] Inventors: Joseph H. Schulman, Los Angeles; Robert F. Moore, Oxnard, both of Calif.

[73] Assignee: Pacesetter Systems, Inc., Sylmar, Calif.

[22] Filed: Jan. 9, 1976

[21] Appl. No.: 647,902

[52] U.S. Cl. ............................. 128/418; 128/419 P
[51] Int. Cl.² ........................................... A61N 1/04
[58] Field of Search ................. 128/418, 404, 419 P

[56] References Cited

UNITED STATES PATENTS

| | | | |
|---|---|---|---|
| 3,216,424 | 11/1965 | Chardack | 128/418 |
| 3,572,344 | 3/1971 | Bolduc | 128/418 |
| 3,749,101 | 7/1973 | Williamson | 128/418 |
| 3,880,169 | 4/1975 | Starr et al. | 128/418 |

FOREIGN PATENTS OR APPLICATIONS

| 311,643 | 8/1971 | U.S.S.R. | 128/418 |
|---|---|---|---|

OTHER PUBLICATIONS

"Longer Pacer Life . . . Ball–Electrode Lead," Cordis Corporation, 1974.

Primary Examiner—Robert W. Michell
Assistant Examiner—Lee S. Cohen
Attorney, Agent, or Firm—Lindenberg, Freilich

[57] ABSTRACT

A myocardial lead for applying electrical pulses to a myocardium includes a relatively large electrode body of a metal, exhibiting high stress fatigue and corrosion resistance properties, a short stud of a metal containing platinum is partially inserted into the electrode body, with the stud portion extending out of the body defining the electrode pin. The stud is electron beam welded to the body. The myocardial lead also includes a distal wire, which consists of a plurality of flexible wire coils of the same metal as the electrode body and are covered by a flexible rubber sleeve. At one end, the wire coils pass through a cavity in the electrode body, with the coils' portion extending therefrom being wrapped around the electrode body and welded thereto. The distal wire extends to a source of electrical pulses. A platinum winding is wrapped around the electrode pin and is attached at one end to the electrode body. A rubber cover is molded around the electrode body and a portion of the distal wire near the electrode body, so that only the electrode platinum pin and several turns of the platinum winding extend therefrom through one side, while the rest of the distal wire extends outwardly from another side of the cover to the source of electrical pulses.

12 Claims, 3 Drawing Figures

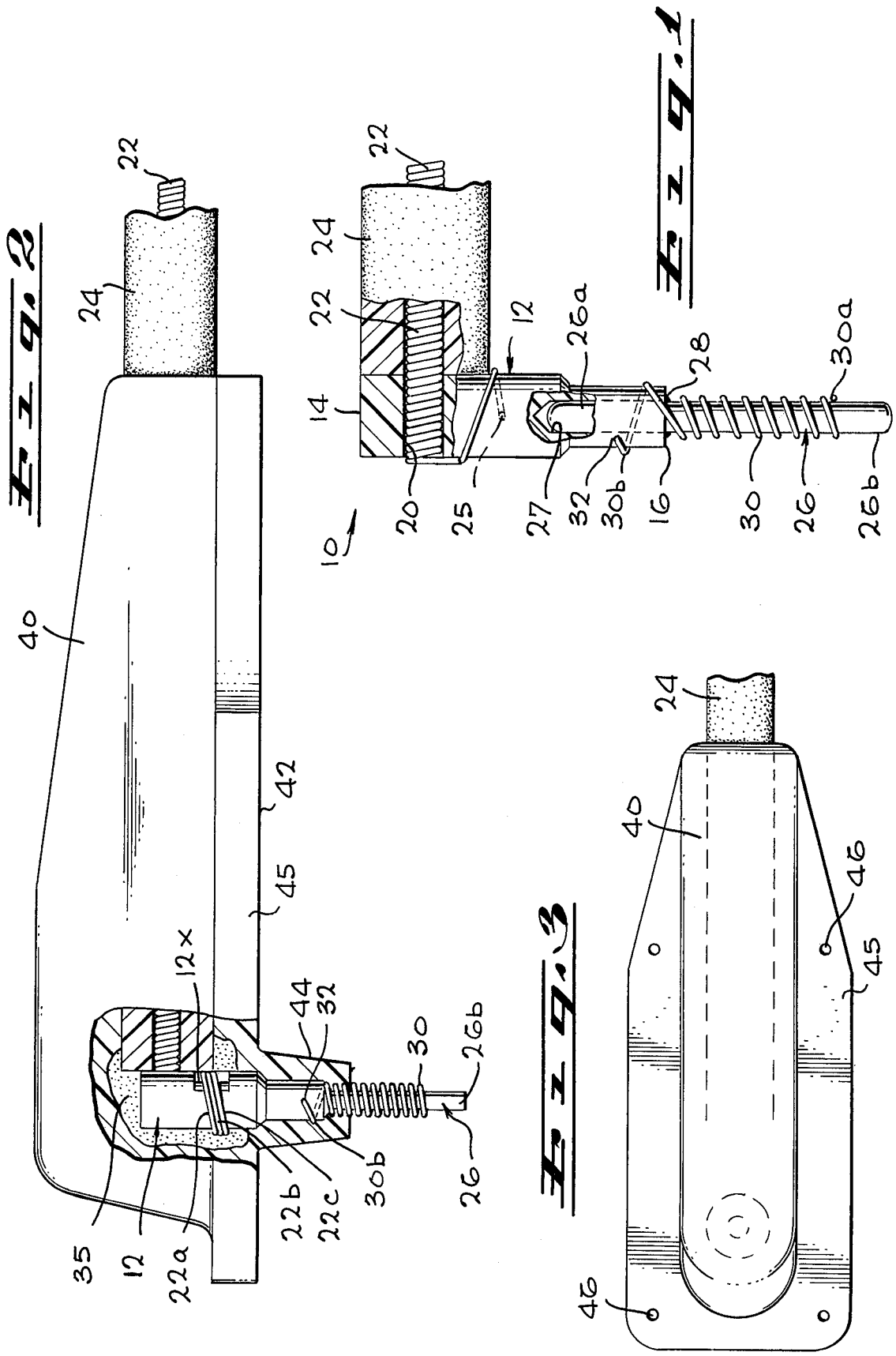

MYOCARDIAL LEAD

BACKGROUND OF THE INVENTION

1. Field of the Invention

The present invention generally relates to heart pulsing means and, more particularly, to an improved myocardial lead.

2. Description of the Prior Art

The use of myocardial leads, in either bipolar or unipolar configurations, to stimulate the surface of a heart by the application of electric pulses is well known. Typically, a myocardial lead consists of an electrode from which a pin extends. The latter is inserted into the myocardium and the electrode is secured to the myocardium. The electrical pulses are supplied to the electrode pin from an appropriate source, typically a pacemaker, through a distal wire, which is connected at opposite ends to the electrode and the pacemaker.

A commercially available myocardial lead consists of an electrode in the form of a bent platinum rod, one end of which serves as the electrode pin. Connected to the other end of the platinum rod, by means of conductive epoxy, is one end of a distal wire. The other end of the distal wire, which is also of platinum, is connectable to a pacemaker. The advantages of using platinum as the electrode pin are well known. Briefly, platinum is biocompatible and furthermore is useful to pass electrical currents either anodially or cathodially into saline solutions, such as those present in the body without corrosion.

The particular prior art myocardial lead has a very significant disadvantage which greatly limits its life and its reliability. As is appreciated, due to heart motion and body movement the myocardial lead has to be able to withstand stress and bending without breaking. This is not attainable with platinum which when subjected to stress, such as a bending force, tends to break quite easily. Experience with the prior art myocardial lead has proven that either the bent platinum electrode and/or the platinum distal wire tend to break when subjected to stress forces, encountered due to heart and/or body motion. Any such break in the lead during use may be fatal to a patient, requiring reliable myocardial stimulation.

OBJECTS AND SUMMARY OF THE INVENTION

An object of the invention is to provide a new improved myocardial lead.

Another object of the invention is to provide a novel myocardial lead designed to practically eliminate the likelihood of fracture due to stresses, to which it may be subjected as a result of heart and/or body motion.

These and other objects of the invention are achieved in a myocardial lead in which the electrode is formed of a relatively large electrode body of an electrically conductive metal with high stress fatigue and corrosion resistance properties. One end of a small platinum rod is inserted into the electrode body and is mechanically and electrically attached thereto. The portion of the platinum rod extending from the electrode body defines the electrode pin. The distal wire of the lead is in the form of a plurality of wire coils of an electrically conductive metal which is very flexible. End portions of the wire coils pass through an opening in the electrode body and are welded thereto. The opposite ends of the wire coils, which are encased in a rubber sleeve, are connectable to a source, e.g., a pacemaker, of electrical pulses, which are transmitted through the coils to the electrode body and therethrough to the platinum pin. Except for the platinum pin, the entire electrode body and a short portion of the wire coils which extend from the electrode body are encased in a molded, rubber flanged cover, which defines a plurality of holes. These holes are used to accommodate sutures, extending from the myocardium, in order to attach the electrode to the myocardium with the pin inserted in an appropriate cut therein.

The novel features of the invention are set forth with particularity in the appended claims. The invention will best be understood from the following description when read in conjunction with the accompanying drawings.

BRIEF DESCRIPTION OF THE DRAWINGS

FIG. 1 is a combination side and cross-sectional view of the major parts of the invention;

FIG. 2 is substantially a side view of one embodiment of the invention, with portions of a rubber cover removed to reveal the internal structure of the invention; and FIG. 3 is a top view of the embodiment, shown in FIG. 2.

DESCRIPTION OF THE PREFERRED EMBODIMENTS

Before describing the details of a specific embodiment of a myocardial lead, which was reduced to practice in accordance with the present invention, attention is first directed to FIG. 1 in which the electrically conductive parts of the novel myocardial lead are shown in a partially side and cross-sectional view. These parts will be described in connection with specific metals which were actually used in the embodiment which was reduced to practice. However, it should be appreciated that other metals may be employed, without departing from the invention.

The novel lead 10 includes a main electrode body 12 which is in the form of a cylinder of an electrically conductive metal, such as nickel alloy, known as MP-35N. Such a metal exhibits well-known high stress fatigue and corrosion resistance properties. In FIG. 1, the top end of body 12 is designated by 14 and its bottom end by 16. The body 12 is essentially cylindrical in shape, except that a portion thereof extending toward the bottom end 16, is of reduced diameter. A hole 20 is formed in the cylindrical body 12 near its top end 14 in a direction perpendicular to the body's longitudinal axis. Accommodated in this hole 20 is a portion of one end of a distal wire 22. The distal wire 22 is encased in a protective rubber sleeve 24, such as silicon rubber, except for the wire portion which extends into and through hole 20. The opposite end of the wire 22 extends to and is connectable to a source of electrical pulses, such as a pacemaker (not shown).

The distal wire 22 consists of several wire coils of an electrically conductive flexible metal such as MP-35N. However, to simplify FIG. 1 only one wire coil is shown. The portion of the wire 22 extending out of hole 20 is wrapped around body 12 and is resistance welded thereto, as represented by 25. Thus, the wire 22 is both mechanically and electrically integrally connected to the electrode body 12.

The novel lead 10 also includes a cylindrical stud 26. The upper portion of the stud, which extends into an axial cavity 27 in body 12 is designated by 26a. Cavity 27 extends inwardly from the bottom end 16 of body 12. The lower portion of the electrode stud 26 which extends from the body 12 through the bottom end 16 is designated by 26b. It is this portion of the stud which represents the electrode pin. Electron beam welding, represented by numeral 28, is used to permanently electrically and mechanically connect the pin-forming stud 26 to the electrode body 12. In practice the stud 26 is preferably electron beam welded to body 12 along the stud portion 26a which is inside the body 12, rather than at the point where the stud extends from the body, as shown in FIG. 1, for explanatory purposes only.

In practice, the electrode pin 26b is inserted into the myocardium to apply the pulses thereto. In order to insure proper contact between the electrode pin and the myocardium, it is desirable to provide a rough surface about the pin so that myocardium tissue is in intimate contact with the pin. This is provided in the lead of the present invention, by surrounding the pin with an elect.ode winding 30 which is wrapped around the pin 26b, and is in intimate contact therewith. The winding 30 is preferably of the same material as pin 26b. The end 30a of winding 30 near the pin tip is not welded to the pin. Rather, it is tightly wrapped around the pin. However, a portion of the winding 30 near the opposite winding end is wrapped around body 12 and its opposite end 30b is welded to the body 12, as represented by 32.

The primary and major advantage of the present invention is the practical elimination of electrode tip fracture due to stress forces created by heart and/or body motion. Except for the short pin 26b, which is of platinum, or a platinum containing alloy, e.g., 90% platinum and 10% iridium, the electrode main body 12, with which the pin is axially aligned, is of a metal with high stress fatigue resistance properties. The body 12 is considerably larger than the pin and therefore it insures the alignement of the pin therein. Furthermore, any flexture stresses to which the electrode body 12 and the pin, inserted therein, are subjected, due to heart motion are transferred by the body 12 to the wire coils of the distal wire 22. Since the wire coils, forming the distal wire 22, are of a flexible metal, e.g., MP-35N, they readily accommodate these flexture stresses due to the heart and/or body motions without breaking. Furthermore, by forming the distal wire 22 of several, e.g., three, wire coils, the reliability of the novel lead is greatly enhanced, since pulses will continue to be supplied through the distal wire to the pin, as long as one of the wire coils is not broken.

It should be pointed out that due to the dissimilarity of the metals of which the pin-forming stud 26 and the electrode body 12 are formed, when in use, galvanic currents flow therebetween. However, since the electrode body 12 is much larger than the stud 26, and body 12 exhibits high corrosion resistance properties, the corrosive effect on the body 12 due to the galvanic currents is very small. Furthermore, any products that may occur as a result of the galvanic corrosion tend to seal off the junction between the dissimilar metals thereby inhibiting any further galvanic flow. Consequently, the novel myocardial lead of the present invention can be used for a very long time without fear of breakage between the body 12 and the pin 26b.

The wire coils of wire 22 are relatively thin and may corrode due to galvanic currents. However, in the present invention most of the galvanic current flows to the body 12 and very little, if any, to the wire coils. Furthermore, by surrounding the wire coils with the rubber sleeve 24, a high impedance is produced between the pin and the wire coils. Thus, direct flow of galvanic current between the pin and the wire coils is further minimized, thereby minimizing if not completely eliminating, the corrosive effect on the wire coils due to any direct flow of galvanic currents thereto. Again, it should be stressed that by forming the distal wire 22 of several wire coils, the breakage of one or more of the coils does not effect the safe performance of the lead 10, as long as at least one of the wire coils remains unbroken.

Attention is now directed to FIG. 2 which is substantially a side and partial cross-sectional view of one embodiment of the invention, which was actually reduced to practice. Therein, the ends of the three wire coils, forming the distal wire 22, which are wrapped around body 12 are designated by 22a, 22b and 22c. If desired, the body 12 may be shaped to form an inwardly extending flat cavity 12x into which the wire coils are wrapped and welded, such as by resistance welding. After welding the wire coils to the body 12 medical adhesive 35 may be used to surround the portion of the body 12 around which the wire coils are wrapped, and the portion of the sleeve 24 which abuts against the body 12.

After inserting the stud portion 26a into cavity 27 of body 12, the stud is electron beam welded to the body 12. Then the winding 30 is wrapped around the pin 26b and the body 12 and its end 30b is welded to the body 12. The latter, together with a portion of sleeve 24, extending from body 12, are encased in a molded rubber cover, which is designated in FIG. 2 by 40. A top view of the cover 40 with a portion of sleeve 24 which extends therefrom is shown in FIG. 3.

As seen from FIG. 2, the cover 40 is molded to form a substantially flat bottom side 42, except for a downwardly directed collar-like portion, hereafter referred to as the collar 44. The latter surrounds the lower portion of body 12 and the part of the winding 30 which is wrapped around it. Thus, only the pin 26b and the winding 30 wrapped around it extend beyond collar 44. As seen from FIG. 3, the molded cover 40 is shaped to form a peripheral flange 45 with several, e.g., four, spaced apart holes 46. The function of these holes is to accommodate sutures which extend from the myocardium and which are used to securely attach the electrode body to the myocardium with the pin 26b inserted in an appropriate cut in the myocardium.

In the embodiment actually reduced to practice, the body 12 consists of a cylindrical rod of length of about 0.235 inch with a diameter of 0.60 inch except that its lower portion of 0.075 in length from its bottom end 16 is of a reduced diameter of about 0.040 inch. The diameter of cavity 27 is on the order of 0.021 inch, and the electrode stud 26 is a platinum cylindrical stud of 0.020 in diameter, and of a length of about 0.325 inch. As previously pointed out, the stud portion 26a extends into cavity 27. After molding the cover 40 only about 0.150 inch of the stud, which forms the pin 26b, extends downwardly out of collar 44. Only about seven ± one turns of winding 30 are exposed around the exposed pin 26b. In use, the exposed pin 26b and the exposed winding 30 extend into the myocardium with the bottom side 42 of cover 40 abutting against the myocardium outer surface.

It should be pointed out that the bottom side of the collar 44 is below the bottom end of body 12 so as to prevent direct contact between the body 12 and the myocardium. Furthermore, by surrounding the lower end of body 12 with collar 44 a significant reduction in the current flow via the saline solution between the pin 26b and the winding 30 on one hand and the body 12 on the other hand is provided. Another advantage of the collar 44 is to limit the area of exposed metal to the myocardium so as to insure proper current density for proper myocardium stimulation.

From the foregoing it should be appreciated that the novel myocardial lead of the present invention comprises a main electrode body of a metal, e.g., MP-35N, which exhibits relatively high stress fatigue and corrosion resistance properties. Supported by this body is an electrically conductive stud, a portion of which extends out of the electrode body and forms the electrode pin, which is inserted into a myocardium to apply the pulses thereto. The stud is preferably of platinum or an alloy containing platinum and is electron beam welded to the electrode body. A distal wire connects the electrode body to a source of electrical pulses, such as a pacemaker.

The distal wire preferably comprises a plurality of wire coils of a flexible metal, e.g., MP-35N. At one of their ends, the wire coils extend through an opening in the electrode body at a point remote from the end from which the pin extends, and are wrapped and welded, such as by resistance welding, to the electrode body. The coils of the distal wire extend from the electrode body to a pacemaker, with the coils being encased in a flexible sleeve of rubber, such as silicon rubber. A cover of molded rubber is formed around the electrode body and a portion of the distal wire, which extends from the electrode body. Only the electrode pin and the winding 30 wrapped around it extend downwardly from the molded cover. The latter has a peripheral flange with several, e.g., four, holes defined in it. These holes are used to facilitate the attachment of the electrode to the myocardium by means of sutures.

To eliminate corrosion-producing galvanic currents between the electrode body and the wire coils, these parts are preferably made of the same metal, e.g., MP-35N. It should be appreciated, however, that other metals, exhibiting the high corrosion and stress fatigue resistance properties may be used. Examples of such metals are stainless steel 316L and elgiloy. Also, the pin need not be formed of pure platinum, but may be formed of a metal alloy containing platinum, e.g., 90% platinum, 10% iridium or titanium, or iridium, as well as other biocompatible metals and which are resistant to corrosion from conducting currents.

It should be pointed out that when using the lead to provide only negative polarity pulses the pin need not be of any of the metals which exhibit resistance to corrosion to pulses of both negative and/or positive polarity, the pin 26b and the winding 30 may be formed of the same metal as the body 12. In such a case the body and the pin may be machined of a single part.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. A myocardial lead for applying pulses to the myocardium, comprising:
    an electrode body of an electrically conductive metal, characterized by relatively high stress fatigue and corrosion resistance properties, said body defining a longitudinal axis and top and bottom ends, a first cavity extending through said body near the body top end and a second cavity extending partially into said body from the bottom end thereof;
    an electrode stud of electrically conductive metal partially extending into said body through said second cavity, with the stud portion extending beyond the electrode body bottom end defining an electrode pin, said stud being mechanically and electrically attached to said body;
    a distal wire formed of a plurality of wire coils of an electrically conductive flexible metal, surrounded by a flexible sleeve with electrical insulating properties, said wire coils extending from a first end, adapted to be connected to a source of electrical pulses, to a second end, the coils extending into said body through the first cavity thereof,
    with portions of said coils up to said second end extending from said first cavity and being wrapped around said body and in mechanical and electrical contact therewith; and
    insulating means in contact with at least the electrode body portion around which said wire coils are wrapped for substantially electrically insulating the wire coils from said electrode pin, except through said body to which the coils and pin-forming stud are attached.

2. The myocardial lead described in claim 1 wherein said electrode body and said wire coils are of the same metal, and the electrode stud is of a different metal.

3. The myocardial lead as described in claim 2 wherein said electrode stud is of a metal containing platinum.

4. The myocardial lead as described in claim 1 wherein said insulating means surround said body with the wire coils wrapped around it and extends over a portion of the sleeve of the distal wire extending outwardly from the first cavity of said body, said insulating means defining an electrode cover with the electrode pin extending outwardly therefrom.

5. The myocardial lead as described in claim 4 wherein said electrode cover defines means for facilitating the attachment of the electrode body to a myocardium with the electrode pin inserted therein.

6. The apparatus as described in claim 4 wherein said electrode cover defines a peripheral flange with a plurality of holes therein, said holes being adapted to accommodate sutures extending from a myocardium with the electrode pin inserted in the myocardium.

7. The myocardial lead as described in claim 4 wherein said electrode stud is of a metal containing platinum, and said electrode body and said wire coils are of a metal containing nickel, with the size of said electrode body being substantially larger than the electrode stud size.

8. The myocardial lead as described in claim 7 wherein said electrode cover defines a peripheral flange with a plurality of holes therein, said holes being adapted to accommodate sutures extending from a myocardium with the electrode pin inserted in the myocardium.

9. The myocardium lead as described in claim 4 further including a wire winding wrapped around said pin from a point near the pin tip, which is most remote from said body, with the opposite end of the wire winding being in contact with and attached to said body, the wire winding being of the same metal as said pin-forming stud.

10. A myocardial lead for applying pulses to the myocardium, comprising:

an electrode body of an electrically conductive metal characterized by relatively high stress fatigue and corrosion resistance properties, said body defining a longitudinal axis and top and bottom ends, and a first cavity extending partially inwardly into said body from said bottom end in a direction parallel with said longitudinal axis;

an electrode stud of an electrically conductive metal, which differs from the electrode body metal, said stud partially extending into said first cavity of said body, and in electrical contact therewith, the stud portion extending beyond the electrode body bottom end defining an electrode pin;

a distal wire formed of a plurality of wire coils of an electrically conductive flexible metal, said wire coils extending from a first end which is adapted to be connected to a source of pulses, to a second end, and a flexible sleeve with electrical insulating properties surrounding said wire coils from the first end up to substantially said second end, at which said coils are mechanically and electrically attached to said body, the wire coils which extend out of said body toward said first end being in a direction substantially perpendicular to said longitudinal axis; and insulating means surrounding said electrode body including the bottom end thereof to prevent direct contact between said electrode body and the myocardium.

11. The myocardial lead as described in claim 10 wherein said electrode body and said wire coils are of the same metal.

12. The myocardial lead as described in claim 11 wherein said electrode stud is of a metal containing platinum.

* * * * *